US010918221B2

(12) United States Patent
Mummaneni

(10) Patent No.: US 10,918,221 B2
(45) Date of Patent: Feb. 16, 2021

(54) ADJUSTABLE SEATING DEVICE BASED ON A SEQUENCE OF BIOMETRIC MEASUREMENTS

(71) Applicant: Mumarba LLC, Austin, TX (US)

(72) Inventor: Reddiah B. Mummaneni, Austin, TX (US)

(73) Assignee: Mumarba LLC, Austin, TX (US)

( * ) Notice: Subject to any disclaimer, the term of this patent is extended or adjusted under 35 U.S.C. 154(b) by 355 days.

(21) Appl. No.: 16/002,859

(22) Filed: Jun. 7, 2018

(65) Prior Publication Data
US 2019/0374043 A1 Dec. 12, 2019

(51) Int. Cl.
| A47C 31/12 | (2006.01) |
|---|---|
| G05B 15/02 | (2006.01) |
| G06F 21/32 | (2013.01) |
| G06F 13/42 | (2006.01) |
| A61B 5/0488 | (2006.01) |
| A47C 7/40 | (2006.01) |
| A47C 3/20 | (2006.01) |
| A47C 1/024 | (2006.01) |
| A47C 7/38 | (2006.01) |
| A47C 7/56 | (2006.01) |
| A47C 1/03 | (2006.01) |

(52) U.S. Cl.
CPC .......... *A47C 31/126* (2013.01); *A61B 5/0488* (2013.01); *G05B 15/02* (2013.01); *G06F 13/4282* (2013.01); *G06F 21/32* (2013.01); *A47C 1/024* (2013.01); *A47C 1/03* (2013.01); *A47C 3/20* (2013.01); *A47C 7/38* (2013.01); *A47C 7/40* (2013.01); *A47C 7/56* (2013.01); *G06F 2213/0042* (2013.01)

(58) Field of Classification Search
CPC ....... A47C 31/126; A47C 3/20; A61B 5/0488; G05B 15/02; G06F 13/4282; G06F 21/32
See application file for complete search history.

(56) References Cited

U.S. PATENT DOCUMENTS 10,078,096 B2 * 9/2018 Fitzsimmons ....... A47C 31/126

FOREIGN PATENT DOCUMENTS

CN 101214143 7/2008

OTHER PUBLICATIONS

Varadhan SKM and Venkatesh Balasubramanian; "Analysis of Muscle Fatigue during Supported and Unsupported Sitting Using Surface Electromyography"; 2006 IET 3rd International Conference on Advances in Medical, Signal and Information Processing—MEDSIP 2006; Jul. 17-19, 2006; four pages.

(Continued)

*Primary Examiner* — Bryan Bui
(74) *Attorney, Agent, or Firm* — Kowert, Hood, Munyon, Rankin & Goetzel, P.C.

(57) ABSTRACT

Devices, systems, and methods for determining a custom ergonomic configuration of an adjustable seating device based on interpretation and analysis of a sequence of biometric measurements of a human subject. An adjustable seating device transitions one or more adjustable surfaces between a sequence of configurations while a human subject is seated in the adjustable seating device and being biometrically measured. A custom configuration is stored in memory, where the custom configuration is a configuration where the biometric measurements of the human subject correspond to a muscle-relaxed state.

20 Claims, 3 Drawing Sheets

(56) References Cited

OTHER PUBLICATIONS

Jeffrey R. Cram and Itamar Vinitzky; Journal of Occupational Rehabilitation, vol. 5, No. 2, 1995; Jun. 1995; 13 pages.
O'Sullivan et al.: "Lumbar posture and trunk muscle activation during a typing task when sitting on a novel dynamic ergonomic chair"; Ergonomics; Sep. 25, 2012; 12 pages.

* cited by examiner

ADJUSTABLE SEATING DEVICE BASED ON A SEQUENCE OF BIOMETRIC MEASUREMENTS

FIELD

The present application relates to seating devices, and more particularly to apparatus, systems, and methods for an adjustable seating device to determine, establish, and transition between configurations resulting in a desired muscular response in one or more users.

DESCRIPTION OF THE RELATED ART

Medical and ergonomic improvements, particularly related to seating devices, are increasingly important. Many people experience muscular and skeletal medical problems resulting from their use of generically designed seating devices. Thus, improvements in the field are desired.

SUMMARY

Embodiments relate to seating devices, systems, and methods to determine a custom configuration of an adjustable seating device based on interpretation and analysis of a sequence of biometric measurements.

According to some embodiments, an adjustable seating system comprises a control module comprising a processor coupled to a memory medium, an adjustable seating device comprising one or more adjustable surfaces, and a biometric measurement system.

In some embodiments, the adjustable seating device may be configured to transition between a sequence of configurations while a human subject is seated in the adjustable seating device. The biometric measurement system may monitor biometric measurements of the human subject during the transitioning. The control module may determine a first configuration of the sequence of configurations during which the biometric measurements of the human subject correspond to a muscle-relaxed state. The control module may store the first configuration in the memory medium.

In some embodiments the adjustable seating device may be configurable according to the first configuration in response to receiving the first configuration and/or in response to user input.

The techniques described herein may be implemented in and/or used with a number of different types of devices, including but not limited to seating devices, computers, cellular phones, tablet computers, wearable computing devices, portable media players, and any of various other computing devices.

This Summary is intended to provide a brief overview of some of the subject matter described in this document. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE DRAWINGS

A better understanding of the present subject matter can be obtained when the following detailed description of various embodiments is considered in conjunction with the following drawings, in which.

Figure 1:
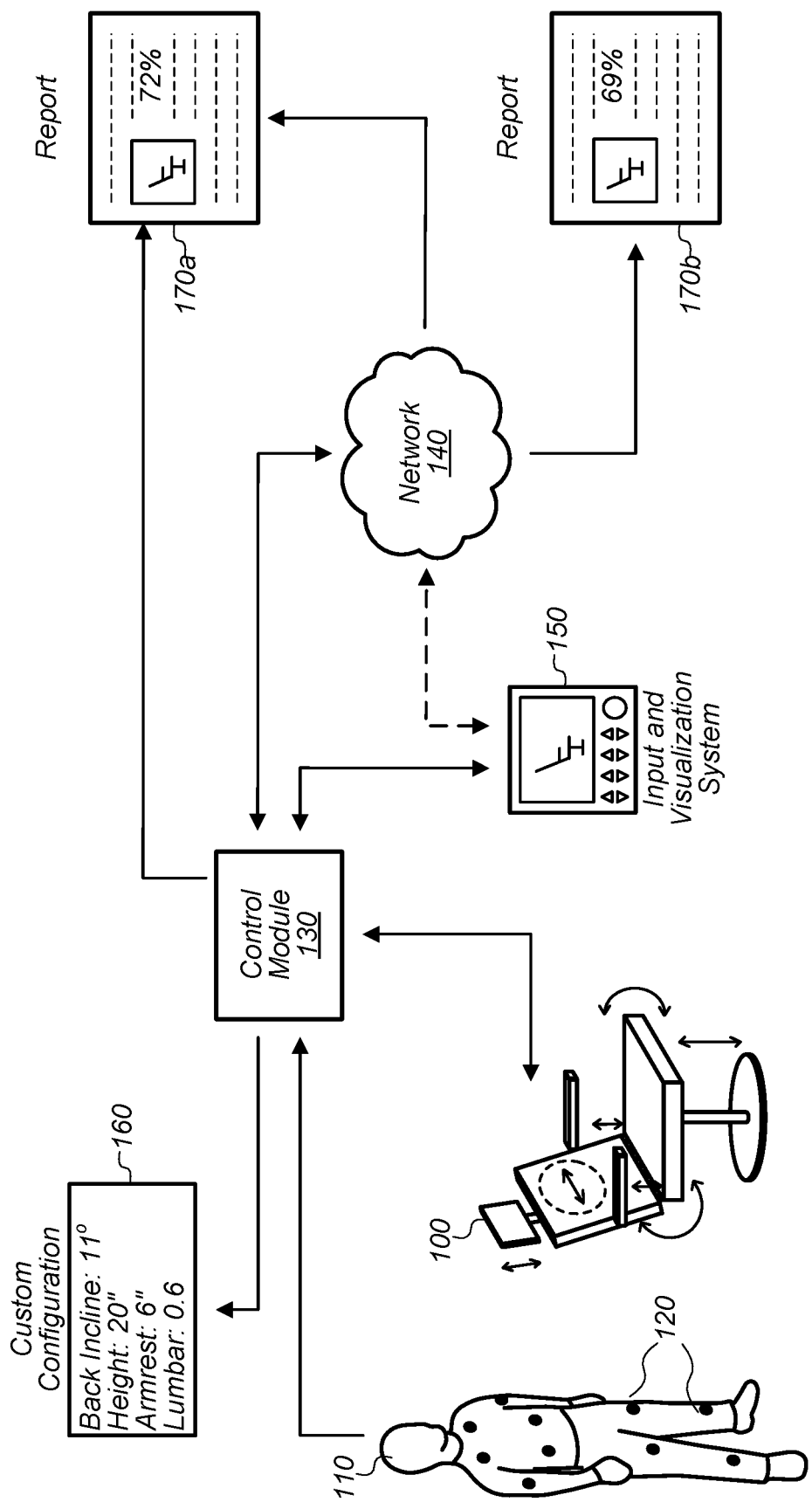
FIG. 1 illustrates an example adjustable seating device and associated systems, according to some embodiments.

While the features described herein may be susceptible to various modifications and alternative forms, specific embodiments thereof are shown by way of example in the drawings and are herein described in detail. It should be understood, however, that the drawings and detailed description thereto are not intended to be limiting to the particular form disclosed, but on the contrary, the intention is to cover all modifications, equivalents and alternatives falling within the spirit and scope of the subject matter as defined by the appended claims.

DETAILED DESCRIPTION

Terms

The following is a glossary of terms used in this disclosure:

Memory Medium—Any of various types of non-transitory memory devices or storage devices. The term "memory medium" is intended to include an installation medium, e.g., a CD-ROM, floppy disks, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. The memory medium may include other types of non-transitory memory as well or combinations thereof. In addition, the memory medium may be located in a first computer system in which the programs are executed, or may be located in a second different computer system which connects to the first computer system over a network, such as the Internet. In the latter instance, the second computer system may provide program instructions to the first computer for execution. The term "memory medium" may include two or more memory mediums which may reside in different locations, e.g., in different computer systems that are connected over a network. The memory medium may store program instructions (e.g., embodied as computer programs) that may be executed by one or more processors.

Portable Memory Device—Any of various types of physical media containing a memory medium, wherein the portable memory device is configured to communicate with a computing device to receive and transmit data from the memory medium. Examples of portable memory devices include universal serial bus (USB) drives, or "thumb drives", portable hard drives, and other types of portable memory media.

Carrier Medium—a memory medium as described above, as well as a physical transmission medium, such as a bus, network, and/or other physical transmission medium that conveys signals such as electrical, electromagnetic, or digital signals.

Processing Element—refers to various elements or combinations of elements that are capable of performing a function in a device, such as a user equipment or a cellular network device. Processing elements may include, for example: processors and associated memory, portions or circuits of individual processor cores, entire processor cores, processor arrays, circuits such as an ASIC (Application Specific Integrated Circuit), programmable hardware elements such as a field programmable gate array (FPGA), as well any of various combinations of the above.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, PASCAL, FORTRAN, COBOL, JAVA, assembly language, etc.; graphical programs (programs written in graphical programming languages); assembly language programs; programs that have been compiled to machine language; scripts; and other types of executable software. A software program may comprise two or more software programs that interoperate in some manner. Note that various embodiments described herein may be implemented by a computer or software program. A software program may be stored as program instructions on a memory medium.

Hardware Configuration Program—a program, e.g., a netlist or bit file, that can be used to program or configure a programmable hardware element.

Program—the term "program" is intended to have the full breadth of its ordinary meaning. The term "program" includes 1) a software program or application which may be stored in a memory and is executable by a processor or 2) a hardware configuration program useable for configuring a programmable hardware element.

Computer System—any of various types of computing or processing systems, including a personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

User Equipment (UE) (or "UE Device")—any of various types of computer systems devices which are mobile or portable and which performs wireless communications. Examples of UE devices include mobile telephones or smart phones (e.g., iPhone™, Android™-based phones), portable gaming devices (e.g., Nintendo DS™ Play Station Portable™, Gameboy Advance™, iPhone™), laptops, wearable devices (e.g. smart watch, smart glasses), PDAs, portable Internet devices, music players, data storage devices, or other handheld devices, etc. In general, the term "UE" or "UE device" can be broadly defined to encompass any electronic, computing, and/or telecommunications device (or combination of devices) which is easily transported by a user and capable of wireless communication. A UE device may be configured to communicate according to various wireless access technologies, including but not limited to cellular communications, Wi-Fi or wireless local area network WLAN communications, short-range wireless access technologies such as Bluetooth, global positioning satellite (GPS) or other global navigational satellite technologies, among other possibilities.

Measurement Device—includes instruments, data acquisition devices, smart sensors, and any of various types of devices that are configured to acquire and/or store data. A measurement device may also optionally be further configured to analyze or process the acquired or stored data. Examples of a measurement device include an instrument, such as a traditional stand-alone "box" instrument, a computer-based instrument (instrument on a card) or external instrument, a data acquisition card, a device external to a computer that operates similarly to a data acquisition card, a smart sensor, one or more DAQ or measurement cards or modules in a chassis. The measurement device may be equipped with one or more sensors for performing electromyographic measurements on a human subject to measure muscle activity, in some embodiments.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Approximately—refers to a value that is almost correct or exact. For example, approximately may refer to a value that is within 1 to 10 percent of the exact (or desired) value. It should be noted, however, that the actual threshold value (or tolerance) may be application dependent. For example, in some embodiments, "approximately" may mean within 0.1% of some specified or desired value, while in various other embodiments, the threshold may be, for example, 2%, 3%, 5%, and so forth, as desired or as required by the particular application.

Concurrent—refers to parallel execution or performance, where tasks, processes, or programs are performed in an at least partially overlapping manner. For example, concurrency may be implemented using "strong" or strict parallelism, where tasks are performed (at least partially) in parallel on respective computational elements, or using "weak parallelism", where the tasks are performed in an interleaved manner, e.g., by time multiplexing of execution threads.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112(f) interpretation for that component.

FIG. 1—Adjustable Seating System

Many variables may impact comfort and physiological consequences of various postures (e.g., seated) and ergonomic factors. For example, adjustments to the position, angle, inclination, or firmness of various elements of a chair may impact muscular activity of a human subject seated in the chair. Due to various differences in the bodies of different human subjects, various adjustments of a chair (e.g., or different chairs) may have different effects on different people. Accordingly, there may be significant benefits to design of custom seating configurations for individuals. In many cases, an ideal or optimized seating configuration may allow a neutral muscular activity state, e.g., so that a human subject's muscles (e.g., skeletal muscles) may be in a relaxed state while seated. However, in other cases there may be benefits to a seating configuration that promotes activation of at least some muscles, for instance in order to provide therapeutic measures to resolve certain muscular or structural problems, such as back pain, etc. Accordingly, it may be useful to measure muscle activation in various positions in order to determine one or more seating configurations that may achieve a desired muscular activity state, e.g., consistent with the goals of an individual in consultation with a medical professional.

FIG. 1 illustrates a simplified example measurement, control, and analysis system, according to some embodiments. It is noted that the system of FIG. 1 is merely one example of a possible system, and that features of this disclosure may be implemented in any of various systems, as desired. In various embodiments, some of the elements shown may be configured, connected, or adjusted in a different position than shown, may be substituted for by other elements, or may be omitted. Additional elements may also be included as desired. As shown, the system may operate as follows.

As shown, the example system includes an adjustable seating device 100 (described in more detail below with respect to FIG. 2). The adjustable seating device 100 can be configured in various ways in order to test different postures of human subject 110. Human subject 110 may sit in the adjustable seating device 100 and one or more configurations of adjustable seating device 100 may be tested. In order to collect data on the one or more configurations, human subject 110 may wear or be attached to one or more sensors 120. Sensors 120 may be or include electromyography (EMG) sensors, among various possibilities. Other types of sensors, e.g., to measure heart rate, blood pressure, imaging sensors, etc., may also be used. Additional sensors (not illustrated) that are not worn by or attached to the human subject 110 may also be used to collect data on the one or more configurations. For example, one or more cameras, weight/pressure sensors, motion sensors, etc. may be used to collect data on the motion or comfort of the human subject 110. Data from the sensors 120 (e.g., illustrated sensors 120 and/or additional sensors) may be provided to a control module 130. Control module 130 may be a computer system, programmable hardware element, or other suitable device. Control module 130 may include one or more programs (e.g., stored and executed locally and/or on network 140, e.g., such programs may be or include internet or cloud-based software) configured to implement techniques disclosed herein. In particular, control module 130 (e.g., and associated software) may be configured to: record, analyze/interpret, and store data from the sensors 120; control the configuration/adjustment of adjustable seating device 100; exchange data with the network 140 (e.g., a local network, company network, and/or the internet) and/or the Input and Visualization System 150; provide data on custom configuration 160 (e.g., a custom seating configuration or ergonomic design); and/or produce reports 170a-170b.

Control module 130 may analyze and interpret data from sensors 120 in combination with configuration information of adjustable seating device 100 and possibly further information about human subject 110. Control module 130 may generate reports 170 (e.g., for a medical professional, human subject 110, etc.) based on the data. Reports 170 may be displayed on input and visualization system 150, printed, or transmitted to a medical professional and/or the human subject 110 over the network 140, among other possibilities. Reports 170 may include data from sensors 120, one or more custom seating configuration designs 160, and/or other information. For example, reports 170 may include results such as the activation level of one or more muscles in one or more seating configurations, e.g., in a custom configuration 160. It is noted that the illustrated values, formats, contents, etc. of custom configuration 160 and reports 170 are exemplary only. In other words, the format and contents (e.g., parameters included) of custom configuration 160 and reports 170 may be configured as desired, e.g., additional or different information may be included, some or all of the illustrated parameters may be omitted, etc., and the values of any parameter may vary, e.g., between various different individual human subjects 110.

Input and visualization system 150 may be used (e.g., by a medical professional, human subject 110, and/or other operator(s)) to visualize configurations of adjustable seating device 100 and/or a custom configuration 160. Input and visualization system 150 may be further used to control adjustable seating device 100, e.g., to adjust one or more parameters of the seating configuration. Input and visualization system 150 may display data from sensors 120 (e.g., an electromyogram). Such data may be displayed in real time, averaged or compared over any desired time period (e.g., comparing multiple configurations of adjustable seating device 100), and/or interpreted data may be displayed. Input and visualization system 150 may connect to (e.g., communicate with) control module 130 directly and/or through network 140. Input and visualization system 150 may be or include a graphical user interface. Although illustrated as a single device, input and visualization system 150 may be or include any number of components, e.g., control panels and/or displays. Some or all portions of input and visualization system 150 may be integrated into (e.g., attached to) adjustable seating device 100, available as a connected or wireless device/display, or manifested virtually as a software component on a network connected computer, tablet, smartphone, etc.

Figure 2:
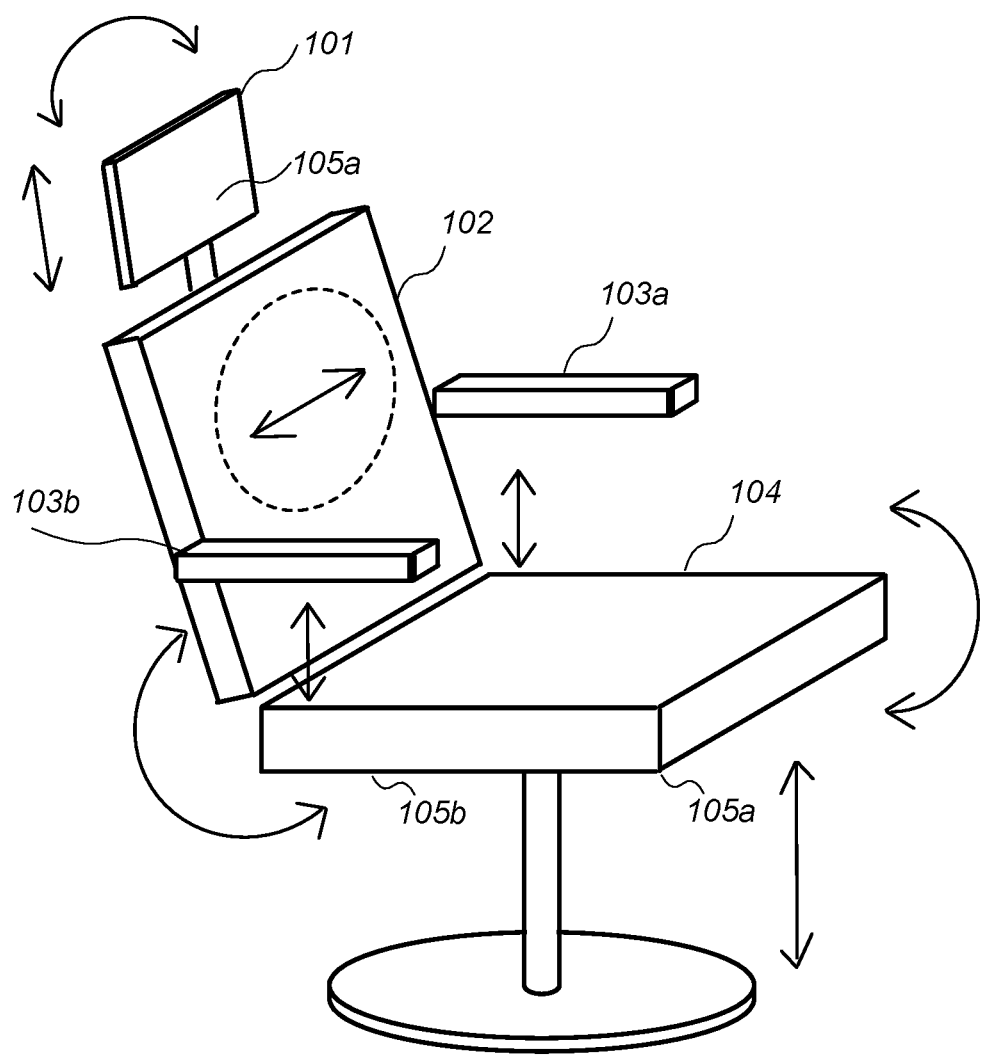
FIG. 2 is a detailed illustration of a particular example of an adjustable seating device, according to some embodiments.

FIG. 2—Adjustable Seating Device

FIG. 2 illustrates adjustable seating device 100, according to some embodiments. It is noted that the adjustable seating device of FIG. 2 is merely one example of a possible device, and that features of this disclosure may be implemented in any of various systems, as desired. For example, other types of devices may be used to evaluate other types of postures, such as an adjustable bed may be used to evaluate laying postures. In various embodiments, some of the elements shown may be configured, connected, or adjusted in a different position than shown, may be substituted for by other elements, or may be omitted. Additional elements may also be included as desired. As shown, the adjustable seating device may operate as follows.

Adjustable seating device 100 may include one or more controls (e.g., manually actuated and/or automatically actuated controls) that allow movement in multiple dimensions for some or all surfaces of the adjustable seating device 100. The controls may allow adjustable seating device 100 to be positioned in multiple configurations for all adjustable surfaces, e.g., adjustments may include heights, angles, inclinations, firmness, tension, resistance, etc.

Headrest 101 may be adjusted up or down (e.g., vertically or adjusting the spacing between the headrest 101 and backrest 102) or angularly (e.g., tilt or incline) as shown. In some embodiments, the curvature of headrest 101 (e.g. vertically and/or horizontally) may be adjustable.

Backrest 102 may be adjusted angularly. Further, backrest 102 may include one or more adjustments related to the spine, e.g., lumbar adjustments. For example, the tension/firmness of one or more portions or areas of backrest 102 may be adjusted in order to provide more or less lumbar support. Other adjustments (e.g., for other parts of the spine) may also be made. Further, backrest 102 may include one or more subcomponents, which may be adjusted individually or in groups. For example, a lower component of the backrest 102 may be adjusted at a different angle and/or firmness than an upper component. the curvature of backrest 102 (e.g. vertically and/or horizontally) may be adjustable.

Armrests 103 may be connected to backrest 102. The armrests 103 may be adjusted vertically, angularly, forward/backward, and/or laterally (e.g., increasing or decreasing the spacing between the armrests).

Seat 104 may be adjusted vertically and angularly (e.g., tilt/inclination). In some embodiments, different portions of seat 104 may be angled independently. Further, the firmness on one or more portions of the seat 104 may be adjusted. The curvature of seat 104 (e.g. side-to-side and/or front-to-back) may be adjustable.

In some embodiments, the adjustable seating device may be one of a variety of other types of seating devices not shown in FIG. 2. The adjustable seating device may be a couch, stool, recliner, bed, or another type of furniture intends to support a human subject.

In some embodiments, the adjustable seating device may comprise a single adjustable surface that is transformable into a variety of configurations (not shown). For example, the adjustable seating device may comprise a singled cushioned surface that is electronically deformable into a variety of different customizable shapes.

Adjustable seating device may further include one or more haptic feedback mechanisms 105*a*-105*b*. The haptic feedback mechanisms 105 may be located in any of various positions, and may be located in positions other than the illustrated locations. The haptic feedback mechanisms 105 may be or include vibrator motors, e.g., to promote feedback to the subject, e.g., to change position or to focus attention on (or away from) one or more muscles/areas. Haptic feedback mechanisms 105 may further be used to promote muscle activity or relaxation, e.g., of specific muscles or in general. For example, haptic feedback mechanisms 105 may promote muscle relaxation through massage, pressure, vibration, temperature, electric stimulus, and/or another stimulus.

FIG. 2 is intended to illustrate one particular example of an adjustable seating device, according to some embodiments. However, it may be appreciated that other types of furniture, such as couches, beds, stools, benches, recliners, vehicle seats, etc., may additionally or alternatively be configured as adjustable seating devices according to embodiments described herein. In these embodiments, one or more surfaces of the particular type of furniture may be variously adjustable according to position, angle, firmness, orientation, etc.

Figure 3:
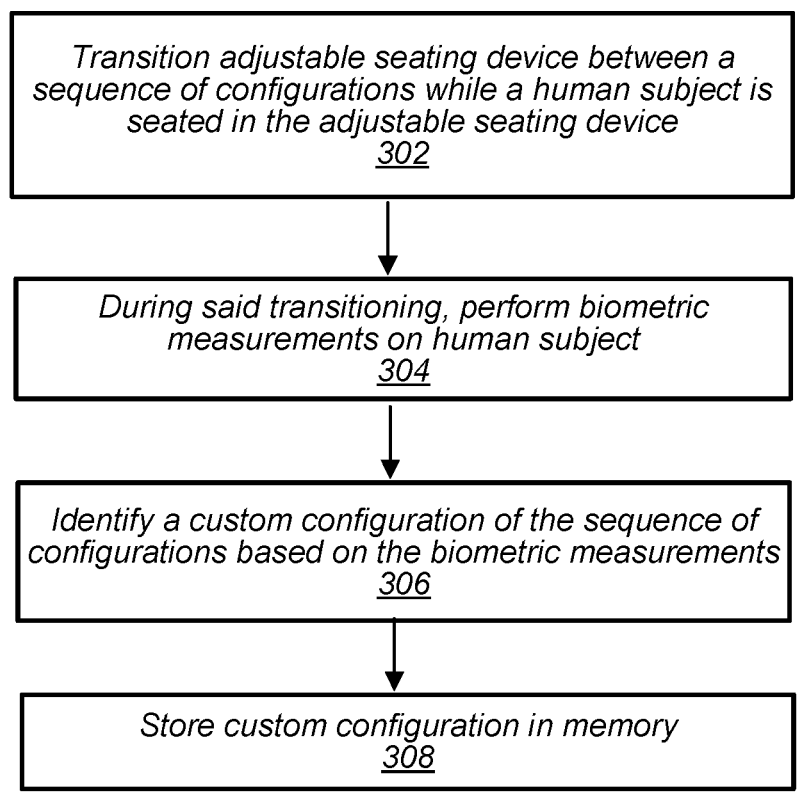
FIG. 3 is a flowchart diagram illustrating an example process for obtaining a custom configuration of an adjustable seating device based on a sequence of biometric measurements, according to some embodiments.

FIG. 3—Method of Measurements and Design

FIG. 3 illustrates an example simplified block diagram of a method for taking measurements to design a custom seating solution, according to some embodiments. Aspects of the method of FIG. 3 may be implemented by a system, such as illustrated in and described with respect to FIGS. 1-2, among other systems and devices, as desired. In various embodiments, some of the elements of the methods shown may be performed concurrently, in a different order than shown, may be substituted for by other method elements, or may be omitted. Additional method elements may also be performed as desired. As shown, the method may operate as follows.

At 302, a human subject 110 may be seated in the adjustable seating device 100 (ASD), and the adjustable seating device may transition between a sequence of configurations. For example, each of one or more adjustable surfaces of the ASD may be transitioned between a sequence of configurations and/or combinations of configurations. In other words, the different configurations of the sequence of configurations may each comprise any combination of configurations of any of the adjustable components of the ASD, as described in greater detail above in reference to FIG. 2.

At 304, during said transitioning of the ASD between the sequence of configurations, measurements (e.g., biometric measurements) may be taken (e.g. using sensors 120) on the human subject. For example, human subject 110 may be seated in the ASD while the ASD is in a particular configuration, and an electromyogram may be generated. In exemplary embodiments, the measurements may be electromyographic measurements taken from sensors applied to a plurality of muscles or muscle groups of the human subject. In other embodiments, other types of biometric measurements may be taken. For example, the sensors 120 may perform skeletal or spinal imaging (e.g., to determine skeletal or spinal configurations of the human subject in various configurations of the ASD); or blood pressure, electrocardiogram, electroencephalogram, or other types of biometric measurements. The measurements may be monitored by the control module. Measurements may be taken in any number of configurations of the ASD, and changes in the measurements in response to the configuration changes may be recorded. For example, measurements may be taken in a first configuration, during a transition to a second configuration, and in the second configuration, etc. Each configuration may be used for any amount of time, e.g., as desired. For example, measurements may be taken in a configuration until a threshold of confidence (e.g., statistical confidence) in one or more measured values is reached, e.g., until a standard deviation threshold is reached, etc. Alternatively or in addition, a continuum of measurements may be made as the ASD is continually transitioned between different configurations. (e.g., an angle of one of the adjustable surfaces of the ASD may be continually transitioned between to values, among other possibilities)

In some embodiments, parameters corresponding to the sequence of configurations and corresponding results of the biometric measurements may be simultaneously displayed on a display coupled to the control module (e.g., input and visualization system 150). Advantageously, a medical professional may be able to utilize the simultaneous display of the parameters and biometric measurement results to help determine which configuration to transition to in order to obtain a desirable muscular activity state.

Adjustments to the configuration may be made automatically (e.g., by control module 130 according to a predetermined algorithm or sequence) and/or in response to input from an operator (e.g., human subject 110 or a medical professional, etc.). The adjustments (i.e., adjustments to the configuration of the ASD leading from one configuration to another) may be made in response to measurement data, e.g., from sensors 120. Adjustments to the configuration may be made to determine a configuration that achieves a desired muscular activity state. The desired configuration may be determined automatically and algorithmically by a processor of the control module, or it may be determined manually under the direction of a medical professional or the human subject. The desired muscular activity state may be a neutral muscular activity state (e.g., or as close to neutral as practicable, e.g., the amount of muscle activity may be reduced). Alternatively, the desired muscular activity state may be a state in which certain (e.g., specific) muscles are active or exhibit certain levels/types of activity. The desired muscular activity state may be determined (e.g., by control module 130 and/or an operator) based on medical or physiological information about the human subject 110 and/or based on measurements from sensors 120. For example, a human subject experiencing lower back pain may desire to sit in a configuration resulting in muscular activity that relieves the lower back pain and/or stimulates muscular activity in a way that is therapeutic for the lower back pain. Further, the desired muscular activity state may be based on subjective assessment (e.g., of comfort) provided by the human subject 110.

Haptic feedback mechanisms 105 may be used to cause human subject 110 to change position and/or change muscle activity. Thus, the activity of the haptic feedback mechanisms 105 may be considered as part of the configuration of the adjustable seating device 100. Alternatively or additionally, measurements may be interpreted in light of the activity of the haptic feedback mechanisms 105, e.g., measurements may be categorized based on whether or not a haptic feedback is active at the time of (or prior to) a time that the measurement was taken.

In some embodiments, one or more measurement techniques may be used simultaneously or sequentially. For example, EMG measurements may be taken in a configuration and other measurements may be taken additionally, e.g., prior to, during, or after the EMG measurements.

The measurements may be analyzed and interpreted (304), e.g., by the control module 130 with or without input from an operator. One or more algorithms may be used to interpret data from the sensors 120, e.g., to determine the muscle response of human subject 110 to the configuration(s) of adjustable seating device 100. Alternatively, a medical professional may analyze and interpret the measurements to determine which configuration results in a desirable muscle response of the human subject, as described in greater detail below at step 306. In some embodiments, offsets or filters may be applied to the measurements, to generate modified measurements. These modified measurements may then be used to determine a custom configuration of the ASD.

In some embodiments, the control module may communicate the sequence of configurations and corresponding results of the biometric measurements to a cloud-based entity over a network. In these embodiments, the cloud-based entity may perform analysis and interpretation on the sequence of configurations and corresponding biometric measurement results to determine a desirable custom configuration of the ASD. The cloud based entity may then communicate the determined custom configuration back to the control module.

The analysis and interpretation of measurements may be performed subsequent to taking measurements and/or concurrently or iteratively with taking measurements. For example, measurements from one or more configurations may be analyzed, and additional configurations may be tested (e.g., measurements taken). Configurations may be repeated one or more times, e.g., in any order.

In some embodiments, the control module may algorithmically undergo different sequences of configurations to determine a particular sequence of configurations that determines a desirable custom configuration (i.e., a custom configuration corresponding to the desired muscle state) in a shorter amount of time. For example, the control module may perform measurements according to different sequences of configurations of the adjustable seating device for a sequence of different human subjects, and the control module may determine a particular sequence of configurations that, on average (e.g., averaged over a plurality of measurement sequences using the particular sequence of configurations), determines a desirable custom configuration in a shorter amount of time. Once determined, the control module may utilize the particular sequence of configurations to more efficiently determine custom configurations for subsequent human subjects.

At 306, based on the analyzed and interpreted measurements during the transition between the sequence of configurations, a custom configuration 160 may be identified, e.g., by control module 130 (306). The custom configuration may be determined based on the configuration of the sequence of configurations that achieved (e.g., most closely approached) the desired muscular state for human subject 110. For example, the custom configuration may be determined to be the configuration of the sequence of configurations for which the muscular activity state of the human subject was the lowest. Alternatively, the custom configuration may be determined to be the configuration for which particular muscles are activated to a desired level of activity (e.g., as determined by a medical professional based on the particular medical needs of the human subject), or for which the human subject experiences a subjectively desired level of comfort. In some embodiments, a heuristic process for determining the custom configuration may be employed, wherein previous results of designing the custom seating configuration may be applied to an analysis of the measurements to determine the custom configuration.

At 308, the control module may store the custom configuration on a memory medium, which may be copied onto a portable memory device (such as a USB drive or other portable memory device) or portable electronic device (such as a user equipment, UE device, a smart phone, a smart wearable device, a tablet, or another type of portable electronic device). Alternatively, the custom configuration may be transmitted over the internet or another network to a location accessible by the human subject. In some embodiments, the custom configuration may be useable by an application, or "app", running on a smart phone or other electronic device. In some embodiments, a dedicated app may be used to organize a user's custom configurations for one or more different types of adjustable seating devices (a user may have separate custom configurations stored on an app for each of an adjustable chair and couch, and/or for adjustable seating devices manufactured by multiple vendors or manufacturers, for example). As described in greater detail below, the human subject 110 may be able to use the custom configuration (whether stored on a portable memory device, a portable electronic device, or an application running on a portable electronic device) to configure one or more adjustable seating devices 100 according to the custom configuration.

In more detail, the custom configuration 160 may be used in any of various ways. In some embodiments, the custom configuration 160 may be used to (e.g., automatically) adjust the configuration of any (e.g., similarly adjustable) furniture. For example, the custom configuration 160 may be used to configure adjustable office chairs, recliners, seats in vehicles, etc. that are designed in accordance with embodiments described herein. The portable memory device (or portable electronic device) with the custom configuration 160 stored thereon may be of a small form factor, such that the human subject 110 may easily carry the portable memory device in various locations. The adjustable seating device 100, as well as other compatibly configured adjustable seating devices, may be configured to couple to the portable memory device (e.g., by insertion of the portable memory device into a customized slot of the adjustable seating device) and read the custom configuration 160.

The adjustable seating device 100 may be configured to adjust its configuration according to the custom configuration. In other words, the ASD may transition its one or more adjustable surfaces according to the custom configuration in response to user input, or automatically in response to receiving the custom configuration, according to various embodiments.

In some embodiments, the ASD may be configured to automatically configure itself according to the custom configuration in response to insertion of (or coupling to) the portable memory device. For example, for embodiments where the portable memory device is a USB drive, the USB drive may be insertable into a USB port of the adjustable seating device to automatically configure the ASD according to the custom configuration.

Alternatively, for embodiments where the portable memory device is a smart phone or other type of portable electronic device, the portable electronic device may be configured to (automatically or in response to user input) communicate with the ASD (e.g., via BlueTooth or another short-range wireless communication technology) to automatically configure the ASD according to the custom configuration. Further, the adjustable seating device may be configured to reconfigure itself according to the custom configuration in response to a determination by the ASD that the portable electronic device is within a predetermined spatial proximity to the ASD. For example, the ASD may determine based on a strength of the short-range wireless signal (or other means) that the portable electronic device is spatially proximate to the ASD. In some embodiments, the ASD may automatically assume the custom configuration based on a determination that the ASD is weight bearing (e.g., because a human subject is seated in the ASD) in addition to a determined proximity of a portable electronic device having stored thereupon the custom configuration. In other words, the ASD may assume the custom configuration if it both detects that a human subject is seated in the ASD and a short-range wireless signal is available that communicates the custom configuration.

In some embodiments, a single ASD may be alternatively used by a plurality of different people, each using different custom configurations of the adjustable seating device. Advantageously, the adjustable seating device may be able to automatically accommodate a plurality of different custom configurations 160 upon communication with different portable memory devices (e.g., portable memory devices owned by different human subjects, and with correspondingly different custom configurations stored thereupon).

Alternatively or in addition, in some embodiments the ASD may have a plurality of custom configurations stored in a memory of the ASD, and each of the plurality of custom configurations may be associated with a respective biometric identifier (such as a fingerprint, weight, etc.). For example, after identifying a custom configuration at step 306, the control module may transmit the custom configuration (with or without an associated biometric identifier) to the ASD, whereupon the ASD may store the custom configuration (and potentially the associated biometric identifier) in a memory. The biometric identifier may be an identifier of the human subject used to obtain the custom configuration. For a sequence of human subjects undergoing the method steps 302-306, the ASD may thereby obtain a plurality of custom configurations.

The ASD may be further configured with a means to detect the respective biometric identifier as biometric identifier input (e.g., it may be equipped with a fingerprint sensor, a weight sensor, etc.). In these embodiments, the ASD may automatically configure itself according to a particular custom configuration upon detection of biometric identifier input matching a biometric identifier associated with a custom configuration stored in memory. As one example, if a human subject sits in the ASD and pressing his/her finger to a fingerprint sensor of the ASD, the ASD may determine if it has stored in memory a custom configuration associated with a matching fingerprint. If it finds a matching fingerprint, the ASD may automatically configure itself according to the associated custom configuration. In various embodiments, each biometric identifier may be unique to a particular human individual (e.g., a fingerprint), or generic to a class of individuals (e.g., a particular weight range of individuals or other generic identifier).

Additionally or alternatively, the custom configuration 160 may be used to (or usable to) design or create a custom furnishing (e.g., chair), with a fixed form or a range of positions based on the interpreted data. Such a custom furnishing may be fabricated in any desired way. For example, a custom chair (e.g., or components of a chair) may be 3-D printed according to precise specifications based on the custom configuration.

Embodiments of the present disclosure may be realized in any of various forms. For example, some embodiments may be realized as a computer-implemented method, a computer-readable memory medium, or a computer system. Other embodiments may be realized using one or more custom-designed hardware devices such as ASICs. Still other embodiments may be realized using one or more programmable hardware elements such as FPGAs.

In some embodiments, a non-transitory computer-readable memory medium may be configured so that it stores program instructions and/or data, where the program instructions, if executed by a computer system, cause the computer system to perform a method, e.g., any of the method embodiments described herein, or, any combination of the method embodiments described herein, or, any subset of any of the method embodiments described herein, or, any combination of such subsets.

In some embodiments, a device (e.g., a control module 130 operating in coordination with adjustable seating device 100 and sensors 120) may be configured to include a processor (or a set of processors) and a memory medium, where the memory medium stores program instructions, where the processor is configured to read and execute the program instructions from the memory medium, where the program instructions are executable to implement any of the various method embodiments described herein (or, any combination of the method embodiments described herein, or, any subset of any of the method embodiments described herein, or, any combination of such subsets). The device may be realized in any of various forms.

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. An adjustable seating device, comprising:
   one or more adjustable surfaces; and
   a memory, wherein the adjustable seating device is configured to:
      for each of one or more respective human subjects:
         transition between a sequence of configurations of the one or more adjustable surfaces while the human subject is seated in the adjustable seating device, wherein biometric measurements of the human subject are obtained by a biometric measurement device during said transitioning, wherein the biometric measurements comprise electromyographic measurements of a plurality of muscles of the human subject; and
         receive a respective custom configuration of the one or more adjustable surfaces corresponding to the human subject, wherein the custom configuration is a particular configuration in the sequence of configurations during which biometric measurements of the human subject correspond to a muscle-relaxed state; and
      store the one or more custom configurations in the memory,
      wherein the adjustable seating device is further configured to transition the one or more adjustable surfaces according to the one or more custom configurations in response to user input.

2. The adjustable seating device of claim 1, wherein the adjustable seating device is further configured to:
   receive a respective biometric identifier associated with each of the one or more custom configurations;
   wherein said user input comprises biometric identifier input, and wherein said transitioning the one or more adjustable surfaces according to the one or more custom configurations comprises transitioning the one or more adjustable surfaces according to a custom configuration of the one or more custom configurations associated with the biometric identifier that matches the biometric identifier input.

3. The adjustable seating device of claim 2,
   wherein the biometric identifier comprises a fingerprint of the respective human subject.

4. The adjustable seating device of claim 2,
   wherein the biometric identifier comprises a weight of the respective human subject.

5. The adjustable seating device of claim 1,
   wherein, for a first custom configuration of the one or more custom configurations, said receiving the first custom configuration comprises receiving the first custom configuration from a portable electronic device via a short-range wireless access technology, and wherein the adjustable seating device is further configured to:
      automatically transition the one or more adjustable surfaces according to the first configuration in response to receiving the first configuration via the short-range wireless access technology.

6. The adjustable seating device of claim 1,
   wherein the adjustable seating device is further configured to:
      communicate with a portable memory device through a universal serial bus (USB) port,
      wherein, for a first custom configuration of the one or more custom configurations, said receiving the first custom configuration comprises receiving the first custom configuration from the portable memory device through the USB port, and wherein the adjustable seating device is further configured to:
   automatically transition the one or more adjustable surfaces according to the first configuration in response to receiving the first custom configuration through the USB port.

7. An adjustable seating system, comprising:
   a control module comprising a processor coupled to a memory medium;
   an adjustable seating device comprising one or more adjustable surfaces; and
   a biometric measurement system, wherein the adjustable seating system is configured to:
      transition, by the adjustable seating device, between a sequence of configurations while a human subject is seated in the adjustable seating device;
      monitor, during said transitioning between the sequence of configurations, biometric measurements of the human subject using the biometric measurement system, wherein the biometric measurements comprise electromyographic measurements of a plurality of muscles of the human subject;
      identify, using the control module, a first configuration in the sequence of configurations during which the biometric measurements of the human subject correspond to a muscle-relaxed state;
      store the first configuration in the memory medium; and
      configure the adjustable seating device according to the first configuration in response to the adjustable seating device receiving the first configuration.

8. The adjustable seating system of claim 7, wherein the adjustable seating system is further configured to:
   store the first configuration on a portable electronic device,
   wherein said receiving, by the adjustable seating device, the first configuration comprises receiving the first configuration from the portable electronic device via a short-range wireless access technology, and
   wherein said configuring the adjustable seating device according to the first configuration in response to said receiving the first configuration is performed automatically.

9. The adjustable seating system of claim 7, wherein said configuring the adjustable seating device according to the first configuration is performed further in response to receiving a biometric identifier that matches a biometric identifier associated with the first configuration.

10. The adjustable seating system of claim 9, wherein the biometric identifier comprises at least one of:
   a fingerprint of the human subject; and
   a weight of the human subject.

11. The adjustable seating system of claim 7, wherein the control module is further configured to:
   simultaneously display, on a display coupled to the control module, parameters corresponding to the sequence of configurations and corresponding results of the biometric measurements;
   wherein said determining the first configuration of the sequence is performed manually by a medical professional.

12. The adjustable seating system of claim 7, wherein the control module is further configured to:
   communicate the sequence of configurations and corresponding results of the biometric measurements to a cloud-based entity over a network;
   wherein said determining the first configuration of the sequence of configurations during which the biometric measurements of the human subject correspond to the muscle-relaxed state comprises receiving, by the control module, the first configuration from the cloud-based entity over the network.

13. The adjustable seating system of claim 7, wherein the control module is further configured to:
   direct the construction of a custom seating device according to the first configuration using a 3-D printing technology.

14. A computer-implemented method for determining a custom configuration of an adjustable seating device, the method comprising:
   directing, by a control module, an adjustable seating device to configure itself according to a sequence of configurations while a human subject is seated in the adjustable seating device;
   monitoring, using a biometric measurement system and during the sequence of configurations, biometric measurements of the human subject, wherein the biometric measurements comprise electromyographic measurements of a plurality of muscles of the human subject;
   determining, by the control module, a first configuration in the sequence of configurations during which the biometric measurements of the human subject correspond to a muscle-relaxed state;
   storing the first configuration as the custom configuration in a memory; and
   configuring the adjustable seating device according to the custom configuration in response to the adjustable seating device receiving the custom configuration.

15. The computer-implemented method of claim 14:
   wherein the memory comprises a portable memory device,
   wherein said receiving, by the adjustable seating device, the custom configuration comprises receiving the custom configuration from the portable memory device, and
   wherein said configuring the adjustable seating device according to the custom configuration is automatically performed in response to said receiving the custom configuration.

16. The computer-implemented method of claim 14, the method further comprising:
   simultaneously displaying parameters corresponding to the sequence of configurations and corresponding results of the biometric measurements on a display;
   wherein said determining the first configuration of the sequence is performed manually by a medical professional.

17. The computer-implemented method of claim 14,
   wherein said determining the first configuration of the sequence of configurations during which the biometric measurements of the human subject correspond to the muscle-relaxed state is automatically and algorithmically performed by a processor of the control module.

18. The computer-implemented method of claim 14, the method further comprising:
   directing the construction of a custom seating device according to the custom configuration using a 3-D printing technology.

19. The computer-implemented method of claim 14,
   wherein said configuring the adjustable seating device according to the custom configuration is performed further in response to the adjustable seating device receiving a biometric identifier that matches a biometric identifier associated with the custom configuration.

20. The computer-implemented method of claim 14,
   wherein the biometric identifier comprises at least one of:
   a fingerprint of the human subject; and
   a weight of the human subject.

* * * * *